United States Patent [19]

Kado et al.

[11] Patent Number: 5,424,201
[45] Date of Patent: Jun. 13, 1995

[54] **METHOD FOR PREPARING AN ANTITUMOR DEXTRAN USING *LACTOBACILLUS CONFUSUS***

[75] Inventors: Hisao Kado; Yasukazu Nakakita, both of Yaizu, Japan

[73] Assignee: Sapporo Breweries Limited, Tokyo, Japan

[21] Appl. No.: 212,295

[22] Filed: Mar. 11, 1994

Related U.S. Application Data

[63] Continuation of Ser. No. 699,259, May 13, 1991, abandoned.

[30] Foreign Application Priority Data

May 31, 1990 [JP] Japan .................... 2-139906

[51] Int. Cl.$^6$ .................... C12P 19/08; C12P 19/04; C08B 37/02
[52] U.S. Cl. .................... 435/103; 435/101; 435/72; 435/823; 536/112; 536/124
[58] Field of Search .................... 435/72, 823, 101, 103; 536/112, 124

[56] References Cited

U.S. PATENT DOCUMENTS

| | | |
|---|---|---|
| 4,396,763 | 8/1983 | Tsuchiya et al. |
| 4,530,903 | 7/1985 | Leuchtenberger et al. ......... 435/130 |
| 4,814,273 | 3/1989 | Brumm et al. ...................... 435/140 |

FOREIGN PATENT DOCUMENTS

| | | |
|---|---|---|
| 1-277484 | 11/1989 | Japan . |
| 1-281073 | 11/1989 | Japan . |
| 2-4714 | 1/1990 | Japan . |
| 3-291232 | 12/1991 | Japan . |
| 2090846 | 7/1982 | United Kingdom . |

OTHER PUBLICATIONS

Patent Abstracts of Japan, vol. 12, No. 283, Aug., 8, 1988, The Patent Office Japanese Government, for JP 63-61002, published Mar. 1988.

Patent Abstracts of Japan, vol. 14, No. 53, Jan. 31, 1990, The Patent Office Japanese Government, for JP 1-281073, published Nov. 13, 1989.

International Journal of Systematic Biology, vol. 30, (USA), Skerman et al "Approved Lists of Bacterial Names", pp. 225–420.

Chemical Abstracts, vol. 71, No. 19, Nov. 10, 1969, abstract No. 88655s, B. F. Hammond, *Arch. of Oral Biol.*, 1969, 14(8), 879–90.

*Primary Examiner*—David M. Naff
*Assistant Examiner*—Francisco C. Prats
*Attorney, Agent, or Firm*—Frishauf, Holtz, Goodman & Woodward

[57] ABSTRACT

*Lactobacillus confusus* strains capable of producing a dextran which has biological activities such as an excellent antitumor activity, etc. are disclosed. Also disclosed is a method for producing said dextran using said microorganism or dextran synthetase prepared by said microorganism.

14 Claims, 3 Drawing Sheets

METHOD FOR PREPARING AN ANTITUMOR DEXTRAN USING *LACTOBACILLUS CONFUSUS*

This is a continuation of application Ser. No. 07/699,259, filed May 13, 1991, now abandoned.

BACKGROUND OF THE INVENTION

1. Field of the Invention

This invention relates to microorganism capable of producing a dextran which has biological activities such as an excellent antitumor activity, etc.; a method for producing said dextran using said microorganism or dextran synthetase prepared by said microorganism.

2. Description of the Prior Art

Methods for preparing antitumor polysaccharides using strains belonging to the genus Lactobacillus have already been disclosed in Japanese Patent Application Laid-Open Nos. 1-281073, 1-277484, 2-4714, etc. However, these are crude products such as cells, capsular polysaccharide or culture broth.

The prior art methods described above provide species of microorganisms which belong to the genus Lactobaccillus but are incapable of producing dextran. The present inventors have found that the dextrans produced by *Lactobacillus confusus* which is a species capable of producing a dextran have an antitumor activity. As a result of extensive investigations, a method for production thereof has been established and the present invention has thus come to be accomplished.

SUMMARY OF THE INVENTION

The present invention relates to a microorganism belonging to *Lactobacillus confusus* and capable of producing a dextran having the properties described below; a method for preparing said dextran and using said microorganism or dextran synthetase produced by said microorganism.

(1) Form: said dextran is a white powder having no taste and no smell;

(2) Solubility: said dextran is soluble in water, formamide and dimethylsulfoxide but insoluble in alcohols, acetone, hexane, chloroform and carbon tetrachloride:

(3) pH of Aqueous Solution: the aquarious solution is neutral or weakly acidic;

(4) Constituent Saccharide: said dextran is composed solely of glucose;

(5) Elementary analysis values: said dextran comprises 43 to 45% of C and 6.0 to 6.3% of H;

(6) Structure:said dextran is an $\alpha$-glucan composed mainly of linear $\alpha$-1,6 glucoside linkages;

(7) Proteins: said dextran contains no protein by the Lowry's method;

(8) Molecular weight: said dextran does not permeate through a dialysis membrane and the molecular weight is presumed to be higher than 10,000 daltons;

(9) Color Reaction: said dextran is positive to anthrone sulfuric acid reaction and phenol sulfuric acid reaction, but negative to biuret reaction, the Lowry-Folin reaction, the Elson-Morgan reaction and idione reaction;

(10) Melting Point: said dextran has no definite melting point;

(11) Ultraviolet Absorption Spectrum: said dextran has no characteristic absorption as shown in FIG. 1;

(12) Infrared Absorption Spectrum: said dextran shows a characteristic absorption of $\alpha$-glucan as shown in FIG. 2;

(13) $^{13}$C-NMR Spectrum: said dextran shows characteristic spectrum of $\alpha$-1,6-glucan as shown in FIG. 3;

(14) Said dextran possesses antitumor activities.

DETAILED DESCRIPTION OF THE PREFERRED EMBODIMENTS

Figure 1:
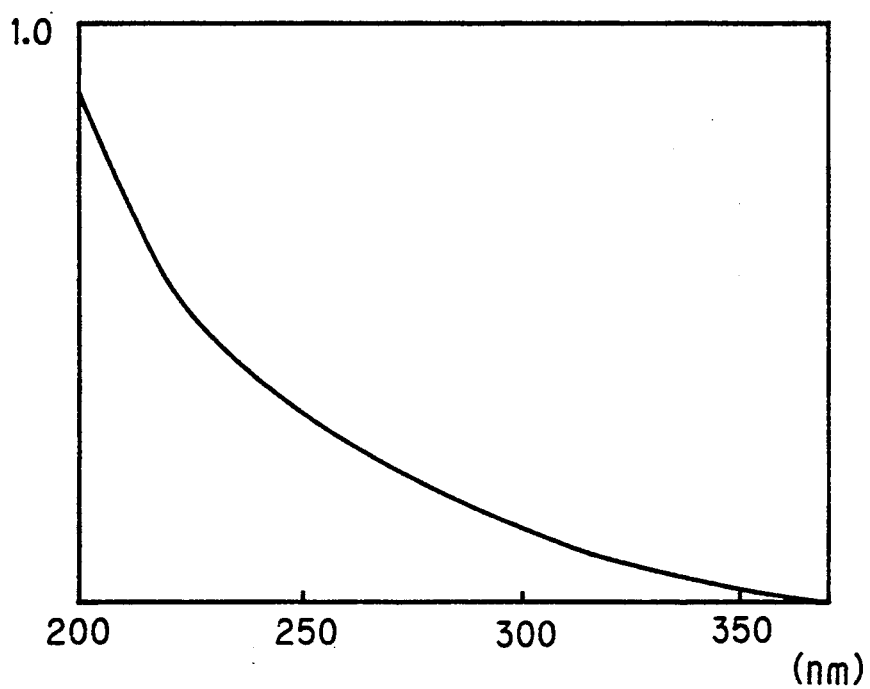
FIG. 1 is UV absorption spectrum of the antitumor dextran obtained in the present invention.

In the present invention, the antitumor dextrans described above may be obtained by culturing a microorganism belonging to *Lactobacillus confusus* and capable of producing a dextran having the properties described above, accumulating a dextran in the culture broth and isolating the dextran. Furthermore, the antitumor dextran may also be obtained by contacting dextran synthetase produced by the microorganism with sucrose and isolating the produced antitumor dextran.

As the microorganism capable of producing an antitumor dextran, there are *Lactobacillus confusus* 40-1 strain, 40-3 strain, 77-1 strain, 78-1 strain and 80-1 strain. Taxonomical properties of these strains are as follows.

TABLE I

| Strain No. | 40-1 | 40-3 | 77-1 | 78-1 | 80-1 |
| --- | --- | --- | --- | --- | --- |
| Gram staining | + | + | + | + | + |
| Morphological characteristic | 0.4 × 1–1.4 Short rod Single, pair Rarely chain | 0.4 × 0.7–1.0 Short rod Single, pair Rarely chain | 0.4 × 0.7–1.6 Short rod Single, pair Chain | 0.4 × 0.7–2.0 Short rod Single, pair Rarely chain | 0.4 × 0.7–1.4 Short rod Single, pair Chain |
| Catalase reaction | − | − | − | − | − |
| Oxidase reaction | − | − | − | − | − |
| Free oxygen demand | Facultative anaerobic | Facultative anaerobic | Facultative anaerobic | Facultative anaerobic | Facultative anaerobic |
| Lactic acid fermentation | Hetero D,L | Hetero D,L | Hetero D,L | Hetero D,L | Hetero D,L |
| Decomposition of arginine | + | + | + | + | + |
| Final pH in a glucose medium | 4.7 | 4.7 | 4.9 | 4.7 | 4.4 |
| Decomposition of esclin | + | + | + | + | ± |
| Dextran production | + | + | + | + | + |

TABLE I-continued

| Strain No. | 40-1 | 40-3 | 77-1 | 78-1 | 80-1 |
|---|---|---|---|---|---|
| Growth in the presence of sodium chloride | | | | | |
| 3.0% NaCl | + | + | + | + | + |
| 6.0% NaCl | − | − | − | − | − |
| Production of acids from carbohydrate | | | | | |
| arabinose | + | + | − | + | ± |
| glucose | + | + | + | + | + |
| fructose | + | + | + | + | + |
| lactose | − | − | − | − | − |
| mannose | + | + | + | + | + |
| treharose | − | − | − | − | − |

Summarizing the foregoing, the strains have the following properties. That is, 1: The microorganisms are positive in gram staining and facultative anaerobic. 2: Shape is short rod. 3: Acid production from trehalose is negative. 4: Lactic acid fermentation is hetero type and lactic acid of both D- and L-forms are produced. 5: Decomposition of arginine is positive. 6: Dextran production is positive.

Therefore, according to Bergey's Manual of Systematic Bacteriology, Vo.1 2 (1986) and Method in Microbiology, Vol. 16, 147–178 (1984), these strains were identified to be *Lactobacillus confusus*. The present inventors named these strains as *Lactobacillus confusus* 40-1 strain (FERM BP-2865), 40-3 strain (FERM BP-2866), 77-1 strain (FERM BP-2867), 78-1 strain (FERM BP-2868) and 80-1 strain (FERM BP-2869), which were deposited at the Fermentation Research Institute, Agency of Industrial Science & Technology, 1–3, Higashilchomes Tsukubanshi, Ibaraki-ken 305 Japan.

These *Lactobacillus confusus* 40-1 strain (FERM BP-2865); 40-3 strain (FERM BP-2866), 77-1 strain (FERM BP-2867), 78-1 strain (FERM BP-2868) and 80-1 strain (FERM BP-2869) are effective for producing the antitumor dextran in view of productivity, etc.

Culture of the microorganism capable of producing the antitumor dextran is, in principle, carried out according to an ordinary microorganism-culture method. However, since *Lactobacillus confusus* is facultative anaerobic, and it demands no oxygen, it is advantageous to adopt stationary culture in liquid medium or gently agitating culture to unify the temperature. Where the antitumor dextran is produced directly in a culture broth, sucrose is essentially required as the carbon source for producing the antitumor dextran. Otherwise, a medium may be one containing nutrient sources the antitumor dextran-producing bacteria can utilize. Any of synthetic media, semi-synthetic media and natural media may be used.

As sucrose which is essentially required as a carbon source, any of crude to purified products of sucrose may be optionally used. For example, refined sugar, black sugar, molasses, blackstrap molasses, saccharose of reagent grade, etc. A concentration of sucrose is 0.5 to 70%, preferably 5 to 50%. As nitrogen sources, there may be used meat extract, peptone, gluten meal, soybean powder, corn steep liquor, dry yeast extract, ammonium sulfate, urea, etc. These nitrogen sources may be used, singly or mixture, and added to medium in a proportion of 0.5 to 5%, preferably 1 to 3%. In addition, phosphoric acid salts, sodium chloride, magnesium salts, cobalt salts, iron salts, etc. may be appropriately added to the medium, if necessary.

The incubation temperature is similar to the culture temperature used for ordinary mesophile bacteria, which is between 15° and 45° C., preferably between 20° and 30° C. The pH in culturing is 5 to 7. The incubation time is 5 to 96 hours, preferably 10 to 24 hours. By culturing under these conditions, the antitumor dextrans can be accumulated in the medium.

Where the antitumor dextrans is produced using dextran synthetase, sucrose is mandatorily required as the carbon source for accumulation of the antitumor dextran synthetase. A concentration of sucrose is preferably 0.1 to 5%. Other conditions for pH, temperature and incubation time are similar to those where the antitumor dextran is obtained directly in a culture broth.

In the thus obtained culture broth, the antitumor dextran synthetase is accumulated intracellulary and extracellularly. Therefore, when the enzyme is recovered from the cells, the broth is ultrasonically treated to disrupt the cells. Alternatively, the enzyme may be extracted from the cells with a surfactant, etc. and the extract is then centrifuged, etc. to remove insoluble matters. Further where the synthetase is recovered from the culture broth, the cells and insoluble matters may be removed by centrifugation, etc. The enzyme can be sufficiently used as a crude enzyme solution for production of the antitumor dextran as it is. If necessary, however, the enzyme may further be purified by dialysis, ultrafiltration, differential fractionation such as gel filtration, etc., salting out with ammonium sulfate, etc., treatments with ion exchange resins, etc., singly or in combination.

By reacting the crude enzyme solution on sucrose, the antitumor dextran can be produced. The reaction is carried out at a temperature of 20° to 45° C., preferably 25° to 35° C. for 5 to 50 hours at pH 5 to 7.

The produced antitumor dextran is usually contained in the medium or in the reaction mixture. Therefore, when the antitumor dextran is produced by fermentation, the antitumor dextran is purified by removing the cells or insoluble matters by means of centrifugation, filtration, etc., then repeating precipitation procedures with polar organic solvents such as methanol, ethanol, propanol, acetone, etc. Further by purifying dialysis, gel filtration, ultrafiltration, treatments with ion exchange resin, activated carbon, etc., singly or in combination, the antitumor dextran of high purity can be obtained. By drying the product through spray drying, freeze drying, precipitation with polar organic solvents, etc., the antitumor dextran can be obtained as a white powder.

Various properties of the anti-tumor dextran obtained by the foregoing procedures are given below.

Figure 2:
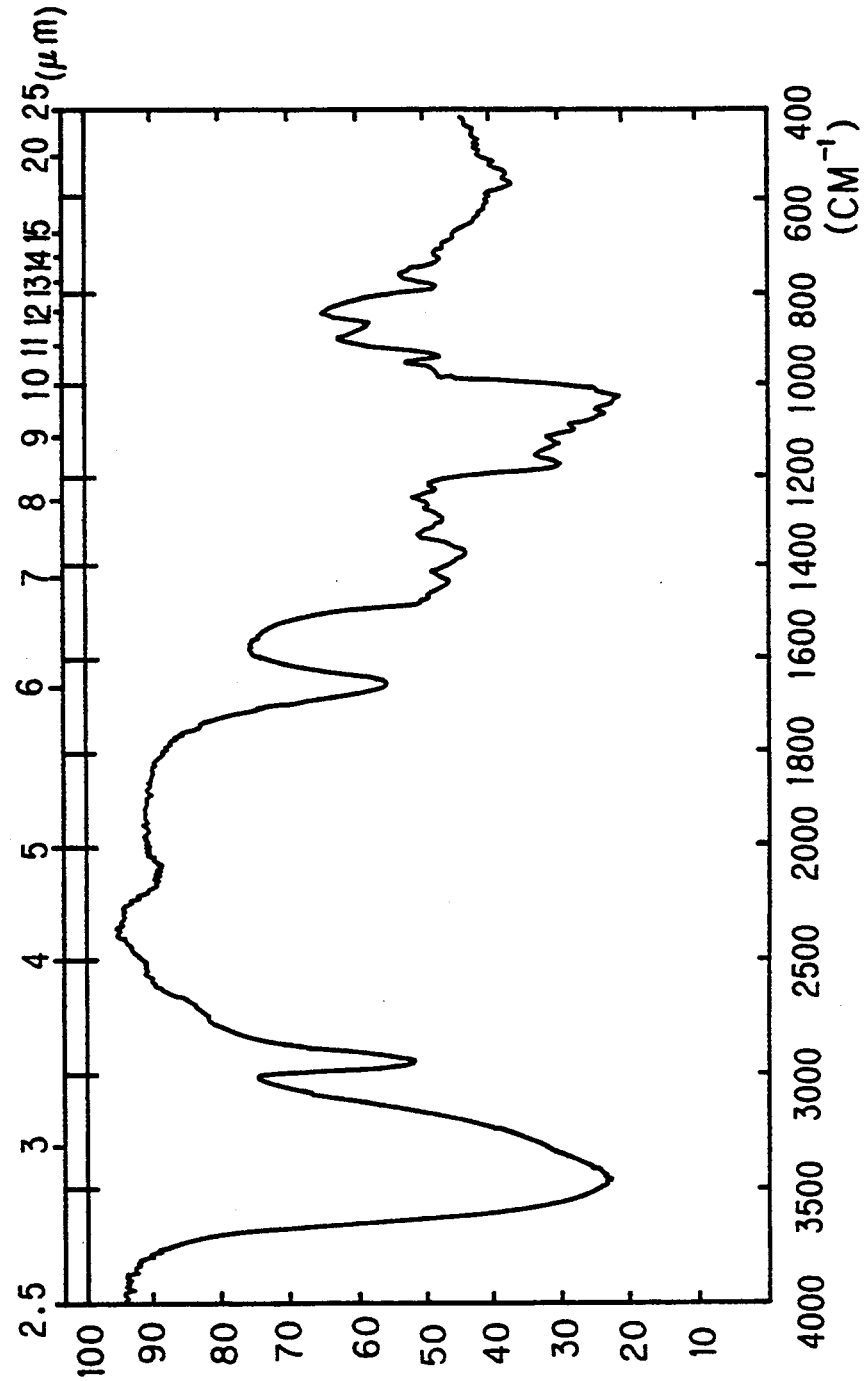
FIG. 2 is IR absorption spectrum of the same substance.

(1) Form: said dextran is a white powder having no taste and no smell;

(2) Solubility: said dextran is soluble in water, formamide and dimethylsulfoxide but insoluble in alcohols, acetone, hexane, chloroform and carbon tetrachloride;

(3) pH of Aqueous Solution: the aquarious solution is neutral or weakly acidic;

(4) Constituent Saccharide: said dextran is composed solely of glucose;

(5) Elementary analysis values: said dextran comprises 43.0 to 45% of C and 6.0 to 6.3% of H;

(6) Structure: said dextran is an α-glucan composed mainly of linear α-1,6 glucoside linkages;

(7) Proteins: said dextran contains no protein by the Lowry's method;

(8) Molecular weight: said dextran does not permeate through a dialysis membrane and the molecular weight is presumed to be higher than 10,000 daltons;

(9) Color Reaction: said dextran is positive to anthrone sulfuric acid reaction and phenol sulfuric acid reaction, but negative to biuret reaction, the Lowry-Folin reaction, the Elson-Morgan reaction and idione reaction;

(10) Melting Point: said dextran has no definite melting point;

(11) Ultraviolet Absorption Spectrum: said dextran has no characteristic absorption as shown in FIG. 1;

(12) Infrared Absorption Spectrum: said dextran shows a characteristic absorption of α-glucan as shown in FIG. 2.

Figure 3:
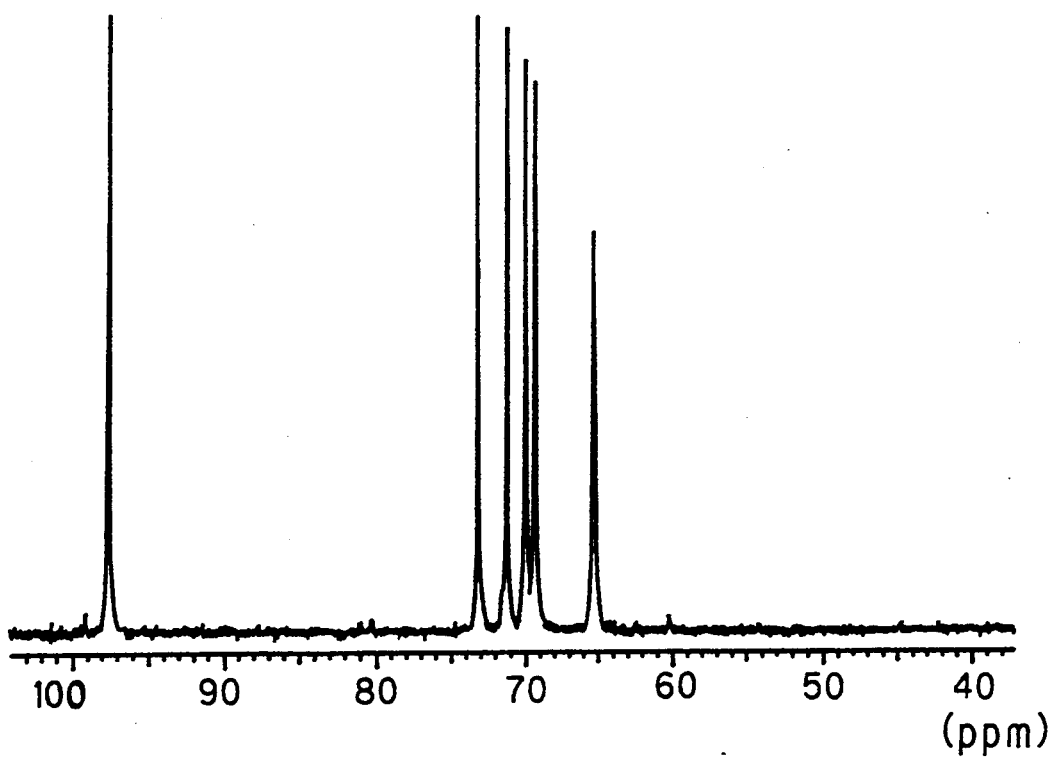
FIG. 3 is $^{13}$C-NMR spectrum of the same substance.

(13) $^{13}$C-NMR Spectrum: said dextran shows characteristic spectrum of α-1,6-glucan as shown in FIG. 3;

(14) Said dextran possesses antitumor activities.

The antitumor dextran obtained in the present invention can be degraded into low molecule through acid hydrolysis by gently heating in a diluted solution of sulfuric acid, hydrochloric acid, formic acid, etc., enzymatic decomposition with a dextran decomposition enzyme, ultrasonication, etc. The antitumor dextran degraded into low molecule can be fractionated by gel filtration, ultrafiltration, etc. to render the molecular weight uniform. It is revealed that among the antitumor dextran degraded into low molecular weight, dextrans having a molecular weight of 10,000 daltons or more has biological activities such as an antitumor activity, etc.

Hereafter a method for assaying the antitumor activity and its results in experiments are given below when there are used the antitumor dextran obtained in Example 1 later described and low molecular products L1 (molecular weight of 1,000,000 or more), L2 (molecular weight of 100,000 to 1,000,000) and L3 (molecular weight of 10,000 to 100,000) of the antitumor dextran obtained in Example 4.

(a) Effect of the antitumor dextrans on syngeneic tumor, Meth-A by intraperitoneal administration Meth-A tumor cells which had been subcultured in the peritoneal cavities of the same syngeneic mouse was intraperitoneally transplanted at a rate of $1 \times 10^5$ cells/mouse to BALB/c-CRJ female mice of 6-week-old having a body weight of 20 g in average. The mice were divided into 4 groups: control group of 20 mice (1 group) and test groups of 10 mice (3 groups). For consecutive 5 days from the next day when the tumor cells were transplanted, the test groups were intraperitoneally administered 0.1 ml each of the solution of the antitumor dextran dissolved in saline at doses of 10, 30 and 100 mg/kg and the control group was similarly given by only saline. Subsequently, the number of survival days was observed and an increased life span was calculated by the following equation.

Increased life span (%) =

$$\frac{\text{Average survival days in the test groups}}{\text{Average survival days in the control group}} \times 100$$

(b) Effect of the antitumor dextran on syngeneic tumor Meth-A by oral administration Meth-A tumor cells which had been subcultured in the peritoneal cavities of the same syngeneic mouse for a week was subcutaneously transplanted at a rate of $6 \times 10^4$ to BALB/c-CRJ female mice of 6 weeks age having a body weight of 20 g in average. The mice were divided into 4 groups: control group of 20 mice (1 group) and test groups of 10 mice (3 groups). For consecutive 10 days from the next day when the tumor cells were transplanted, the test-groups were administered orally using an oral sonde by 0.2 ml each of a saline solution of the antitumor dextran at doses of 10, 30 and 100 mg/kg and the control group was similarly given by only physiological saline. 35 Days after the tumor cells were transplanted, each mouse was killed and the propagated tumor was cut out and the weight was measured. The inhibition ratio was calculated based on the following equation.

Inhibition ratio (%) =

$$\left(1 - \frac{\text{Average weight of tumor in test groups}}{\text{Average weight of tumor in control group}}\right) \times 100$$

The effects of the antitumor dextran assayed by the methods (a) and (b) described above are shown in Table II.

TABLE II

| Dose | (a) Intraperitoneal administration | | (b) Oral administration | |
|---|---|---|---|---|
| | Average number of survival day (day) | Increased life span (%) | Average weight of tumor (g) | Inhibition ratio (%) |
| Control (physiological saline) | 18.7 | — | 12.10 | — |
| Anti-tumor dextran: | | | | |
| 10 mg/kg | 31.0 | 166 | 7.01 | 42 |
| 30 mg/kg | >42.0 | >225 | 5.03 | 58 |
| 100 mg/kg | 32.2 | 172 | 5.54 | 54 |

From the above table, it is revealed that the antitumor dextran possesses a potent antitumor activity with the optimum dose of about 30 mg/kg, both. by intraperitoneal administration and by oral administration.

Next, with respect to L1, L2 and L3 which are low molecular products of the antitumor dextran, the experiments similar to (a) and (b) described above were carried out in a dose of 30 mg/kg. The results are shown in Table III.

TABLE III

| Dose | (a) Intraperitoneal administration | | (b) Oral administration | |
|---|---|---|---|---|
| | Average number of survival day (day) | Increased life span (%) | Average weight of tumor (g) | Inhibition ratio (%) |
| Control (physiological saline) | 18.7 | — | 12.10 | — |
| L1 (30 mg/kg) | >42.0 | >225 | 5.13 | 58 |
| L2 (30 mg/kg) | >42.0 | >225 | 5.72 | 53 |
| L3 (30 mg/kg) | >42.0 | >225 | 5.90 | 51 |

From the above table, it is revealed that the antitumor dextran degraded into low molecule by partial hydrolysis also retained the antitumor activity almost comparable to that prior to hydrolysis.

It is also confirmed that the antitumor dextran and its hydrolysate exhibit an excellent antitumor activity against syngeneic tumor Lewis lung tumor, melanoma B-16, allogeneic tumor sarcoma 180, Ehrlich tumor, etc., by intraperitoneal administration or oral administration in a dose range of 10 to 100 mg/kg.

Next, acute toxicity of the antitumor dextran and its low molecular products L1, L2 and L3 will be described. Using ten 5-week-old male SD-CRJ rats having a body weight of 120 to 150 g as one group, the antitumor dextran, L1, L2 and L3 were orally administered to rats at a dose of 15 g/kg, which was the physical administration limit. During observation, no death of rats was noted and body weight increase was the same as that in the control group. In addition, no abnormally was noted at all in appearance and necropsy. Accordingly, it is considered that $LD_{50}$ would be larger than 15 g/kg and there would be no acute toxicity.

On the other hand, when the antitumor dextran was intravenously administered, $LD_{50}$ 280 mg/kg. And in case of L1, L2 and L3, their toxicity decreased with decrease of their molecular weight. In the case of L3, $LD_{50}$ was larger than 5 g/kg, and no toxicity was noted. Accordingly, the low molecular antitumor dextran has very advantageous properties when (it is) used an injection drug.

For the practical production of medicines, the antitumor dextran or L1, L2 and L3 are used to produce medicines such as liquid, pills, tablets, powders, granules, suppositories, etc., singly or in combination with a variety of excipients (water, physiological saline, polyethylene glycol, glycerol, gelatin, starch, dextrin, cellulose, lactose, mannitol, etc.).

In addition, the antitumor dextran may also be used as beverages or foodstuffs in functional foods for purposes of prevention of diseases or health care, or as food additives, since the antitumor dextran has a variety of biological activities useful for maintaining health through oral administration and is readily processed because of tasteless and odorless nature.

[Examples]

Next, the present invention is described in more detail by referring to the examples.

Example 1

(Culture)

Cells obtained from stab culture of *Lactobacillus confusus* 40-1 strain (FERM BP-2865) were inoculated into 5 ml of medium (2.0% of sucrose, 0.5% of yeast extract, 2.0% of $K_2HPO_4$, pH 7.4) in a test tube of 15 mm in diameter, the stationary culture was carried out at 26° C. for 24 hours. Then, 5 ml of the medium was inoculated on 400 ml of medium having the same composition in an 500 ml Erlenmeyer's flask, and the stationary culture was carried out at 26° C. for 24 hours.

The obtained culture broth, 400 ml, was inoculated on 20 liters of SM1 medium (10% of sucrose, 0.05% of yeast extract, 0.5% of $K_2HPO_4$, 0.1% of sodium chloride, pH 7.4) in a 30 liters jar fermenter. While gently agitating (0.2 v/v/m, 10 rpm) at 26° C. for 15 hours in a nitrogen flow, cultivation was carried out.

(Purification)

After adjusting pH of culture broth to 7, the medium was heated at 100° C. for the purpose of sterilization. Then, the cells and insoluble matters were removed with a continuous centrifuging machine to give 18.6 liters of the culture supernatant.

Methanol was gradually added to the culture supernatant with agitating, in a final concentration of 45% (v/v) and the mixture was allowed to stand. After the supernatant was removed by decantation, the resulting precipitates were washed with 60% (v/v) methanol. The precipitates were dissolved in 20 liters of deionized water again. The precipitation with methanol and washing with 60% (v/v) methanol were performed 3 times in total. Then by spray drying 270 g of the antitumor dextran was obtained as a white powder.

Example 2

Culture and purification were performed in a same manner as in Example 1 except that blackstrap molasses was added to SM1 medium in a concentration of 10% instead of sucrose. The resulting precipitates were dissolved in 3 liters of deionized water. Then by freeze drying, 251 g of the antitumor dextran was obtained as a white powder.

Example 3

Methanol was gradually added with agitating to 100 ml of the culture supernatant obtained in Example 1 in a final concentration of 45% (v/v). After the obtained glutinous precipitates were washed with 60% (v/v) methanol, the precipitates were dissolved in 100 ml of deionized water again. The solution was passed through DEAE TOYOPEARL 650 M ® which had been equilibrated with deionized water. The non-absorbed fraction was collected and concentrated. After desalting and then freeze drying, 1.1 g of the antitumor dextran was obtained.

Example 4

After 5.0 g of the antitumor dextran powder obtained in Example 1 was dissolved in 500 ml of 2% sulfuric acid, the solution was partially hydrolyzed at 60° C. for 4 hours. After neutralizing with barium carbonate, the precipitates were removed by centrifugation. Ultra filtration was performed using membranes of 1,000,000, 100,000 and 10,000 for fractionation of molecular weights in this order to give 3 fractions of L1, L2 and L3, namely, L1 (molecular weight of 1,000,000 or more), L2 (molecular weight of 100,000 to 1,000,000) and L3 molecular weight of 10,000 to 100,000), respectively. By freeze drying each fraction, the low molecular antitumor dextran of L1: 1.6 g, L2: 1.2 g and L3: 0.9 g were obtained, respectively as a white powder.

Example 5

The procedures were performed in a same manner as in Example 1 except that *Lactobacillus confusus* 40-3 strain (FERM BP-2866) was used instead of *Lactobacillus confusus* 40-1 strain (FERM BP-2865). Thus, 263 g of the antitumor dextran was obtained as a white powder.

Example 6

The procedures were performed in a same manner as in Example 1 except that *Lactobacillus confusus* 77-1 strain (FERM BP-2867) was used instead of *Lactobacillus confusus* 40-1 strain (FERM BP-2865). Thus, 212 g of the antitumor dextran was obtained as a white powder.

Example 7

The procedures were performed in a same manner as in Example 1 except that *Lactobacillus confusus* 78-1 strain (FERM BP-2868) was used instead of *Lactobacillus confusus* 40-1 strain (FERM BP-2865). Thus, 250 g of the antitumor dextran was obtained as a white powder.

Example 8

The procedures were performed in a same manner as in Example 1 except that *Lactobacillus confusus* 80-1 strain (FERM BP-2869) was used instead of *Lactobacillus confusus* 40-1 strain (FERM BP-2865). Thus, 209 g of the antitumor dextran was obtained as a white powder.

Example 9

Cells obtained from stab culture of *Lactobacillus confusus* 40-1 strain (FERM BP-2865) were inoculated on 5 ml of medium (2.0% of sucrose, 0.5% of yeast extract, 2.0% of $K_2HPO_4$, pH 7.4) in a test tube of 15 mm in diameter, and stationary culture was carried out at 26° C. for 24 hours.

Then, 5 ml of the medium was inoculated on 400 ml of medium having the same composition in an 500 ml Erlenmeyer's flask, and stationary culture was carried out at 26° C. for 17 hours. The obtained medium was centrifuged (10,000 G, 15 minutes) to give 360 ml of the supernatant. The supernatant was concentrated by ultrafiltration membrane (Amicon ®, hollow fiber, fractional molecular weight of 10,000) and then replaced by 5 mM acetate buffer (pH 5.5) to give 100 ml of the crude enzyme solution. After adding a small quantity of toluene, the crude enzyme solution was stored at 4° C.

After 20 ml of the obtained crude enzyme solution was mixed with 60 ml of 50 mM acetate buffer (pH 5.5) in which 8 g of sucrose had been dissolved, a small quantity of toluene was added to the mixture. The mixture was gently agitated at 30° C. for 15 hours. Methanol was added to the resulting viscous solution in a final concentration of 40% (v/v) to precipitate the antitumor dextran.

After washing with 60% (v/v) methanol, the obtained precipitates were dissolved in 80 ml of deionized water again. The precipitation with methanol and washing with 60% (v/v) methanol were repeated. After dissolving in deionized water and freeze drying, 3.2 g of the antitumor dextran was obtained as a white powder.

Example 10

After 10 g of sucrose was dissolved in 100 ml of the culture supernatant obtained in Example 9, a small quantity of toluene was added to the solution. While mildly agitating, the solution was kept at 30° C. for 18 hours. 150 ml of methanol was added with stirring to the resulting viscous solution (final concentration of 43%) to give glutinous precipitates. After washing with 60% (v/v) methanol, the precipitates were dissolved in 100 ml of deionized water again. The precipitation with methanol and washing with 60% (v/v) methanol (v/v) were repeated. After dissolving in deionized water and freeze drying the solution, 3.9 g of the antitumor dextran was obtained as a white powders.

Example 11

Cells obtained from stab culture of *Lactobacillus confusus* 40-1 strain (FERM BP-2865) were inoculated on 5 ml of medium (2.0% of sucrose, 0.5% of yeast extract, 2.0% of $K_2HPO_4$, pH 7.4) in a test tube of 15 mm in diameter the stationary culture was carried out at 26° C. for 24 hours. Then, 5 ml of the medium was inoculated on 400 ml of medium having the same composition charged in an 500 ml Erlenmeyer's flask, and stationary culture was carried out at 26° C. for 17 hours.

After the cells in the culture broth (350 ml) was disrupted with a ultrasonic homogenizer, insoluble matters were removed by centrifugation to give 330 ml of the supernatant. The resulting supernatant was treated in a same manner to Example 9 to give 80 ml of the crude enzyme solution. After 20 ml of the obtained crude enzyme solution was mixed with 100 ml of 50 mM acetate buffer (pH 5.5) in which 12 g of sucrose had been dissolved, a small quantity of toluene was added to the solution. The mixture was mildly agitated at 30° C. for 15 minutes. Methanol was added to the resulting viscous solution in a final concentration of 40% to precipitate the antitumor dextran. After washing with 60% (v/v) methanol, the precipitates were dissovled in 120 ml of deionized water again. The precipitation with methanol and washing with 60% (v/v) methanol (v/v) were repeated. After dissolving in deionized water and freeze drying, 5.0 g of the antitumor dextran was obtained as a white powder.

Example 12

The procedures were performed in a same manner as in Example 9 except that *Lactobacillus confusus* 40-3 strain (FERM BP-2866) was used instead of *Lactobacillus confusus* 40-1 strain (FERM BP-2865). Thus, 2.7 g of the anti-tumor dextran was obtained as a white powder.

Example 13

The procedures were performed in a same manner as in Example 9 except that *Lactobacillus confusus* 77-1 strain (FERM BP-2867) was used instead of *Lactobacillus confusus* 40-1 strain (FERM BP-2865). Thus, 2.1 g of the antitumor dextran was obtained as a white powder.

Example 14

The procedures were performed in a same manner as in Example 9 except that *Lactobacillus confusus* 78-1 strain (FERM BP-2868) was used instead of *Lactobacillus confusus* 40-1 strain (FERM BP-2865). Thus, 2.4 g of the antitumor dextran was obtained as a white powder.

Example 15

The procedures were performed in a same manner as in Example 9 except that *Lactobacillus confusus* 80-1 strain (FERM BP-2869) was used instead of *Lactobacillus confusus* 40-1 strain (FERM BP-2865). Thus, 3.4 g of the antitumor dextran was obtained as a white powder.

The antitumor dextran of the present invention which is a pure glucan, has biological activities such as an excellent antitumor activity, etc. and has no toxicity can be stably prepared by a simple and efficient method.

What is claimed is:

1. A process for preparing an antitumor dextran which comprises
    (a) culturing a microorganism belonging to *Lactobacillus confusus* selected from the group consisting of strain FERM BP-2865, strain FERM BP-2866, strain FERM BP-2867, strain FERM 2868 and strain FERM BP-2869 in a culture broth comprising a carbon source containing sucrose and a nitrogen source, said microorganism having an ability of producing a dextran having the following properties:
        (1) Form: said dextran is a white powder having no taste and no smell;
        (2) Solubility: said dextran is soluble in water, formamide and dimethylsulfoxide, but insoluble in alcohols, acetone, hexane, chloroform and carbon tetrachloride;
        (3) pH of Aqueous Solution: the aqueous solution is neutral or weakly acidic;
        (4) Constituent Saccharide: said dextran is comprised solely of glucose;
        (5) Elementary analysis values: said dextran comprises 43 to 45% of C and 6.0 to 6.3% of H;
        (6) Structure: said dextran is an $\alpha$-glucan comprised mainly of linear $\alpha$-1,6 glucoside linkages;
        (7) Proteins: said dextran contains no protein by the Lowry's method;
        (8) Molecular weight: said dextran does not permeate through a dialysis membrane and the molecular weight is considered to be higher than 10,000 daltons;
        (9) Color Reaction: said dextran is positive to anthrone sulfuric acid reaction and phenol sulfuric acid reaction, but negative to biuret reaction, the Lowry-Folin reaction, the Elson-Morgan reaction and the idione reaction;
        (10) Melting Point: said dextran has no definite melting point;
        (11) Ultraviolet Absorption Spectrum: said dextran has no characteristic ultraviolet absorption;
        (12) Infrared Absorption Spectrum: said dextran shows a characteristic absorption of $\alpha$-glucan;
        (13) $^{13}$C-NMR Spectrum: said dextran exhibits a characteristic spectrum of $\alpha$-1,6-glucan;
        (14) said dextran possesses antitumor activities; and
    (b) collecting said dextran from the culture broth.
2. The process according to claim 1, wherein the culture broth further comprises one or more of a phosphoric acid salt, sodium chloride, a magnesium salt, a cobalt salt or an iron salt.
3. The process according to claim 2, wherein the culture broth comprises sucrose, a nitrogen source, a phosphoric acid salt, sodium chloride, a magnesium salt, a cobalt salt and an iron salt.
4. The process according to claim 1, wherein the culturing is carried out at an incubation temperature of 15° to 45° C.
5. The process according to claim 1, wherein the culturing is carried out at a pH of 5 to 7.4.
6. The process according to claim 1, wherein the culturing is carried out for an incubation time of 5 to 96 hours.
7. The process according to claim 3, wherein the carbon source is sucrose in a concentration of 0.5 to 70%.
8. The process according to claim 3, wherein the culturing is carried out at an incubation temperature of 15° to 45° C.
9. The process according to claim 3, wherein the culturing is carried out at a pH of 5 to 7.4.
10. The process according to claim 3, wherein the culturing is carried out for an incubation time of 5 to 96 hours.
11. The process according to claim 4, wherein the culturing is carried out at a pH of 5 to 7.4.
12. The process according to claim 4, wherein the culturing is carried out for an incubation time of 5 to 96 hours.
13. The process according to claim 1, wherein the culturing is carried out at a pH of 5 to 7.
14. The process according to claim 1, wherein the culturing is carried out at a pH of 7.4.

* * * * *